(12) United States Patent
Marks et al.

(10) Patent No.: US 8,218,152 B1
(45) Date of Patent: Jul. 10, 2012

(54) GROUP REFRACTIVE INDEX RECONSTRUCTION WITH BROADBAND INTERFEROMETRIC CONFOCAL MICROSCOPY

(75) Inventors: Daniel L. Marks, Chapel Hill, NC (US); Stephen A. Boppart, Champaign, IL (US); Adam M. Zysk, Chicago, IL (US); Simon C. Schlachter, Wilmette, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 601 days.

(21) Appl. No.: 12/326,974

(22) Filed: Dec. 3, 2008

Related U.S. Application Data

(60) Provisional application No. 60/992,180, filed on Dec. 4, 2007.

(51) Int. Cl.
*G01B 11/02* (2006.01)

(52) U.S. Cl. .......... 356/497; 356/479; 356/517

(58) Field of Classification Search .......... 356/479, 356/497, 517, 451, 456
See application file for complete search history.

(56) References Cited

U.S. PATENT DOCUMENTS

| | | | | |
|---|---|---|---|---|
| 5,737,084 A | * | 4/1998 | Ishihara | 356/609 |
| 5,956,355 A | * | 9/1999 | Swanson et al. | 372/20 |
| 6,002,480 A | * | 12/1999 | Izatt et al. | 356/479 |
| 6,172,752 B1 | * | 1/2001 | Haruna et al. | 356/503 |
| 6,525,875 B1 | * | 2/2003 | Lauer | 359/371 |
| 7,009,712 B2 | | 3/2006 | Hill | |
| 2005/0057756 A1 | * | 3/2005 | Fang-Yen et al. | 356/497 |
| 2005/0088663 A1 | * | 4/2005 | De Groot et al. | 356/497 |
| 2005/0128488 A1 | * | 6/2005 | Yelin et al. | 356/496 |
| 2007/0087445 A1 | * | 4/2007 | Tearney et al. | 436/172 |

OTHER PUBLICATIONS

Joris J. J. Dirckx, Liesbeth C. Kuypers and Willem F. Decraemer, Refractive index of tissue measured with confocal Microscopy; University of Antwerp, Laboratory of Biomedical Physics, Belgium; Journal of Biomedical Optics 10(4), 044014 Jul./Aug. 2005.

A. Drechsler, M. A. Lieb, C. Debus and A. J. Meixner, Confocal microscopy with a high numerical aperture parabolic mirror, Physikalische ChemieUniversität Siegen, Germany; Dec. 3, 2001, vol. 9, No. 12, Optics Express.

(Continued)

*Primary Examiner* — Tarifur Chowdhury
*Assistant Examiner* — Michael P Lapage
(74) *Attorney, Agent, or Firm* — Sunstein Kann Murphy & Timbers LLP

(57) ABSTRACT

A system and method for microscale measurement and imaging of the group refractive index of a sample. The method utilizes a broadband confocal high-numerical aperture microscope embedded into an interferometer and a spectrometric means, whereby spectral interferograms are analyzed to compute optical path delay of the beam traversing the sample as the sample is translated through the focus of an interrogating light beam. A determination of group refractive index may serve to disambiguate phase ambiguity in a measurement of refractive index at a specified wavelength. Spatial resolution of object characterization in three dimensions is achieved by imaging the object from multiple viewpoints.

14 Claims, 5 Drawing Sheets

OTHER PUBLICATIONS

Ilko K. Ilev and Ronald W. Waynan, Kimberly R. Byrnes, Juanita J. Anders, t, Dual-confocal fiber-optic method for absolute measurement of refractive index and thickness of optically transparent media; , Center for Devices and Radiological Health, U.S. Food and Drug Administration, Maryland; Department of Anatomy, Physiology and Genetics, Uniformed Services University of the Health Sciences, Maryland; Oct. 1, 2002 / vol. 27, No. 19 / Optics Letters.

L. Lepetit, G. Chériaux and M. Joffre, Linear techniques of phase measurement by femtosecond spectral interferometry for applications in spectroscopy, Laboratoire d Optique Appliquée, Ecole Nationale Supérieure de Techniques Avancées, Ecole Polytechnique, Unité de Recherche Associée au Centre National, de la Recherche Scientifique 1406, F-91120 Palaiseau, France, vol. 12, No. 12, Dec. 1995/J. Opt. Soc. Am. B.

N.M. Dragomir, X.M. Goh and A. Roberts, Three-Dimensional Refractive Index Reconstruction With Quantitative Phase Tomography; School of Physics, The University of Melbourne, Australia; Microscopy Research and Technique (2007).

Wonshik Choi, Christopher Fang-Yen, Kamran Badizadegan, Seungeun Oh, Niyom Lue, Ramachandra R. Dasari and Michael S. Feld, Tomographic phase microscopy; Department of Pathology, Harvard Medical School and Massachusetts General Hospital, Boston, Massachusetts 02114; G.R. Harrison Spectroscopy Laboratory, MIT, Cambridge, MA; Published Online Aug. 12, 2007; DOI:10.1038/NMETH1078.

Andrei V. Zvyagin, K. K. M. B. Dilusha Silva, Sergey A. Alexandrov, Timothy R. Hillman and Julian J. Armstrong, Refractive index tomography of turbid media by bifocal optical coherence refractometry; Optical + Biomedical Engineering Laboratory, School of Electrical, Electronic & Computer Engineering, The University of Western Australia; Dec. 15, 2003, vol. 11, No. 25, Optics Express.

Adam M. Zysk, Daniel L. Marks, Dianna Y. Liu and Stephen A. Boppart, Needle-based reflection refractometry of scattering samples using coherence-gated detection, Biophotonics Imaging Laboratory, Beckman Institute for Advanced Science and Technology, Department of Electrical and Computer Engineering, University of Illinois; Apr. 16, 2007, vol. 15, No. 8, Optics Express.

Adam M. Zysk, Daniel L. Marks, P. Scott Carney and Stephen A. Boppart, Contrast Enhancement and Artifact Reduction for Projected Index Computed Tomography, Department of Electrical and Computer Engineering, Beckman Institute for Advanced Science and Technology, University of Illinois, Copyright 2004.

Adam M. Zysk, J. Josh Reynolds, Daniel L. Marks and P. Scott Carney, Projected index computed tomography, Department of Electrical and Computer Engineering, Beckman Institute for Advanced Science and Technology, University of Illinois, May 1, 2003 / vol. 28, No. 9 / Optics Letters.

Yuuki Watanabe and Ichirou Yamaguchi, Geometrical tomographic imaging of refractive indices through turbid media by a wavelength-scanning heterodyne interference confocal microscope, Optical Engineering Laboratory, RIKEN (The Institute of Physical and Chemical Research, Japan; Applied Optics / vol. 41, No. 13 / May 1, 2002.

Tyler S. Ralston, Daneil L. Marks, P. Scott Carney and Stephen A. Boppart, Interferometric synthetic aperture microscopy, Institute for Advanced Science and Technology, University of Illinois; nature physics I vol. 3 Feb. 2007.

Maciej Wojtkowski, Vivek J. Srinivasan, Tony H. Ko, James G. Fujimoto, Andrzej Kowalczyk and Jay S. Duker, Ultrahigh-resolution, high-speed, Fourier domain optical coherence tomography and methods for dispersion compensation; Department of Electrical Engineering and Computer Science and Research Laboratory of Electronics Massachusetts Institute of Technology; May 31, 2004 / vol. 12, No. 11 / Optics Express.

* cited by examiner

GROUP REFRACTIVE INDEX RECONSTRUCTION WITH BROADBAND INTERFEROMETRIC CONFOCAL MICROSCOPY

CROSS-REFERENCE TO RELATED APPLICATIONS

The present application claims priority from Provisional Application Ser. No. 60/992,180, filed Dec. 4, 2007, which is incorporated herein by reference in its entirety.

STATEMENT REGARDING FEDERALLY SPONSORED RESEARCH OR DEVELOPMENT

The present invention has been developed, in part, with Government support under Contract Number R01 EB005221, awarded by the National Institutes of Health. The Government has certain rights in the invention.

TECHNICAL FIELD

The present invention relates to confocal microscopy, advantageously used, for example, in the optical characterization of biological objects. More particularly, the present invention relates to broadband interferometric systems and methods of determining refractive index attributes of a sample.

BACKGROUND ART

Nondestructive characterization of biological tissue often employs light-tissue interaction. More particularly, the refractive index of tissue is often a valuable component of tissue analysis. Recent studies have shown, for example, that refractive index variations have potential diagnostic capability in distinguishing cancerous breast tissue. Studies have also emphasized the importance of refractive index variations due to changes in biochemical environment. For instance, it has been shown that in common medical practice oxygen saturation modulates the refractive index of hemoglobin, thus affecting the optical measurement of blood oxygenation.

Several methods have been proposed to measure refractive index in biological tissue, but all have specific limitations. Both optical coherence tomography (OCT) and confocal scanning laser microscopy (CSLM), for example, are used for non-destructive subsurface optical imaging of tissue, but suffer from depth-dependent distortions caused by inhomogeneities of the refractive index in the sample and of the medium surrounding the sample. Bifocal optical coherence refractometry (BOCR), for example, which tomographically maps the refractive index based on an interferometric measurement of a distance between two foci that are scanned depth-wise through a sample, relies on measurement of light backscattered by the sample, but is limited by the non-uniformity of such scattering. Methods of measuring refractive index by confocal microscopy (CM), using the difference (between the nominal focus position and actual focus position) induced by index of refraction variation, suffers, particularly, from low resolution in the direction of optical axis of the confocal microscope. Moreover, most interferometric techniques are known to be extremely susceptible to mechanical vibrations.

To date, understanding of the refractive index properties of cellular structures is, in some respects, limited by the challenges confronting its direct measurement in situ, and further improvement of imaging capabilities is highly desirable.

SUMMARY OF THE INVENTION

Embodiments of the present invention provide methods and systems for imaging and characterizing a sample, positioned at a focus of a confocal microscope. Characteristics that may be determined with the embodiments of the invention include a group refractive index and, in particular, a three-dimensional distribution of a groups refractive index.

In some embodiments, sample-imaging methods include illuminating successive volume elements of a sample with light from a polychromatic source, e.g. an infrared light, interfering a sample beam of light collected from each successive volume element positioned at the focus with a reference beam of light derived from the source to form a recombined beam for producing successive interferograms respectively corresponding to successive volume elements, and cross-correlating the sample beam and the reference beam to derive data representing relative phase delay of light traversing the sample. In a specific embodiment, the fractional bandwidth of the illuminating light may be at least 2 percent. Recombination of the sample beam and the reference beam may be performed interferometrically, e.g., by positioning the confocal microscope within an arm of an interferometer. The sample beam may be collected in transmission through the sample. The recombined beam may be spatially filtered, for example with a low-pass filter that is telecentric in image and object spaces. In some embodiments, the derivation of the data may include spectrally resolving the successive interferograms with a phase-detection member (such as a spectrophotometer) and deconvolving the successive interferograms. The derived data, representing relative phase delay, may include data representing spectral dependence of phase of the sample beam of light. According to some embodiments, the relative phase delay of light traversing the sample is free of phase-wrapping ambiguity, and imaging the group refractive index may include reconstructing a three-dimensional distribution of the group refractive index, whether at multiple wavelengths or a single wavelength.

Alternative embodiments of the invention provide a method for optical microscopic investigation of a sample, the method comprising disposing the sample at a focus of a confocal microscope, the confocal microscope embedded within a sample arm of an interferometer; focusing light from a source onto the sample to form a sample beam in transmission through the sample, a portion of light passing through a reference arm of the interferometer to form a reference beam; varying mutual positioning of the sample and the focus so as to have broadband light successively illuminate different portions of the sample; and interfering the sample beam and the reference beam to form position-dependent confocal interferometric images. The method may further include spatially filtering the position-dependent confocal interferometric images with a low-pass filter, the low-pass filter being telecentric in object and image spaces. The illuminating light may generally be broadband light, e.g., with a fractional bandwidth of at least 2 percent. In a specific embodiment, the sample is illuminated with infrared light and at high numerical aperture (e.g., exceeding 0.75). In another embodiment, the method may additionally include applying, in a computer process, three-dimensional deconvolution algorithm to data representing the position-dependent confocal interferometric images to derive optical path delay through the sample. In a specific embodiment, both arms of the interferometer may be characterized by substantially identical optical dispersion.

Related embodiments disclose an interferometric confocal microscope configured for transmission imaging of the sample, where the microscope includes one or more objectives containing an off-axis paraboloidal section such as, e.g., the reflecting paraboloidal section. In some of the embodiments, the microscope may operate in an immersion medium.

Additionally or in alternative, embodiments of the invention provide for an interferometric apparatus that includes an interferometer with at least one arm, a source of light generating a beam (portions of which are coupled into arms of the interferometer to produce an output beam forming an interferogram), an off-axis paraboloidal reflector positioned within an arm of the interferometer, and a phase-detection member adapted to resolve a spectrally-dependent spatial characteristic of a sample by acquiring and analyzing an interferogram derived from the sample. In a specific embodiment, the phase-detection member may be a spectrophotometer. The output beam may be additionally spatially filtered, e.g., in order to leave only a single spatial mode of light in the beam. In specific embodiments where the interferometer has more than one arm, the optical dispersion characteristics of the interferometric arms may be substantially identical. Furthermore, the off-axis paraboloidal reflector may operate in immersion.

Additional embodiments of the invention provide a computer program product for use on a computer system for imaging the group refractive index of a sample. Such computer program product includes a tangible storage medium having a computer readable program code thereon, where the computer readable program code includes
  a. program code for storing interferometric data representing interferograms obtained by positioning successive volume elements of a sample at the focus of a confocal microscope; and
  b. program code for determining relative positions of the focus of the confocal microscope within the sample from interferometric data.

In some embodiments, program code for determining relative positions of the focus may include program code for deriving a measure of relative phase delay of light traversing the sample. Furthermore, the program code for deriving the measure of relative phase delay of light traversing the sample may include a program code for determining spectral dependence of phase of light collected at each relative position of the focus.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
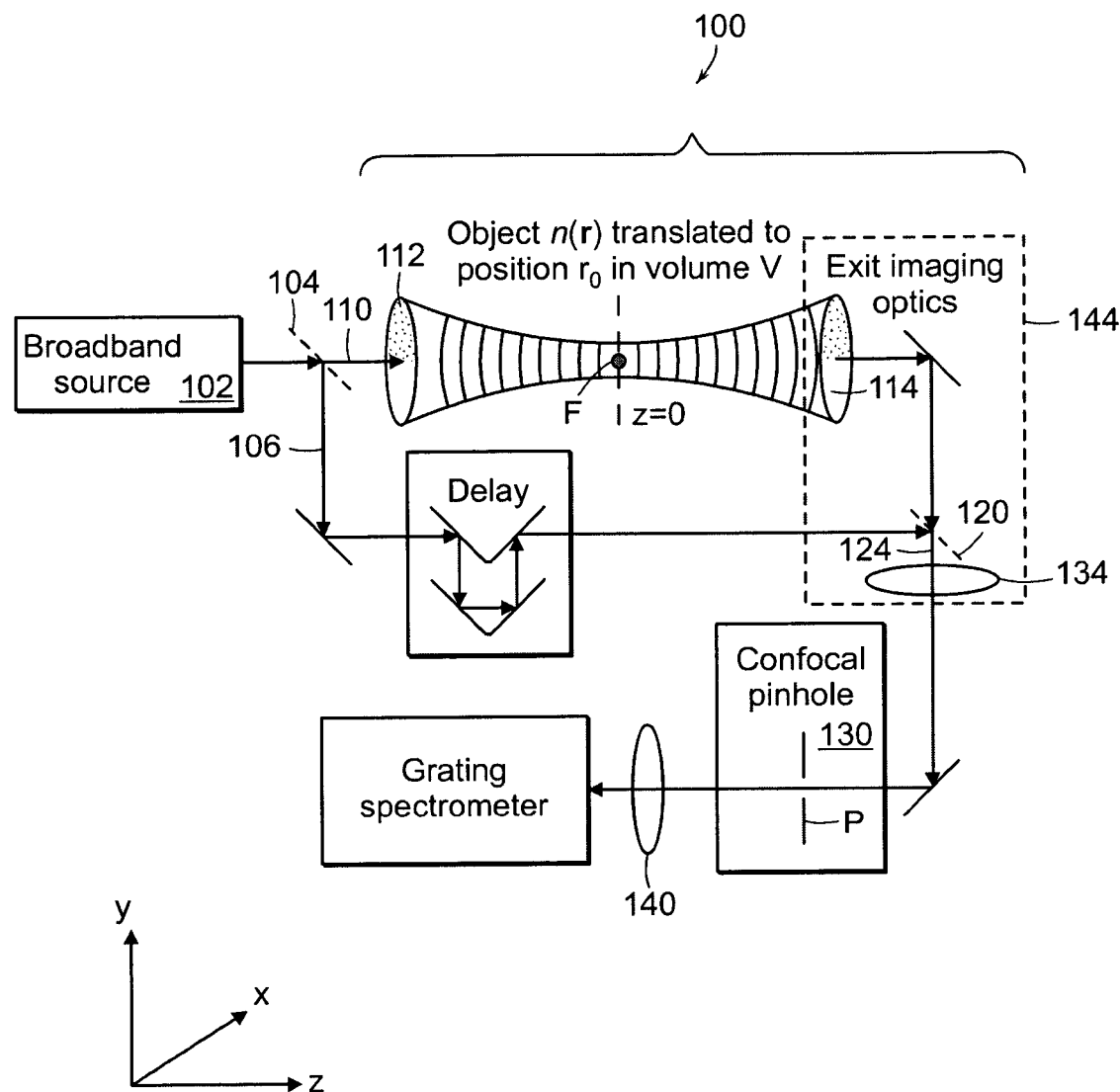
FIG. 1 schematically illustrates an optical path through interferometric confocal microscope for measuring a group refractive index according to an embodiment of the present invention.

Embodiments of the invention describe a new instrument and methods for imaging the group refractive index of a medium. This instrument combines confocal microscopy with spectral interferometry so that the phase delay of light propagating through the medium can be precisely measured at each point in the medium. Because spectral inteferometry measures relative phase between frequencies in a single interferogram snapshot, embodiments of the present invention are advantageously far less susceptible to vibrations, source intensity noise, and do not require phase unwrapping.

Preferred embodiments of the present invention, rather than conventionally relying on characterization of light backscattered from a sample, instead determine a refractive index from direct measurements of the group delay of the light transmitted through the sample. Analysis of a perturbation expansion of the eikonal of a wavefront as a function of the refractive index shows that the changes in time, of light ray travel through the medium, that are first order in the index perturbation are independent of perturbations in the ray direction. This is a consequence of Fermat's principle and is the basis of travel time tomography and projection index computed tomography (PICT). Because one is expecting to measure very small amounts of optical path delay variation when passing a ray through individual cellular organelles (10-200 nm additional path delay), a method that is insensitive to perturbation of the ray path is required.

Confocal microscopy typically uses high numerical aperture focusing. Tight focusing implies that the illumination beam should more properly be regarded as a converging cone of rays rather than a single ray. Therefore, a solution for traveltime tomography for high numerical aperture illumination cannot be based on the assumption that illumination is a pencil beam.

In accordance with preferred embodiments of the present invention, a transmission confocal microscope is embedded in a Mach-Zehnder interferometer, and spectral interferometric detection is employed. Spectral interferometric detection is described, for example, in Lepetit et al., "Linear techniques of phase measurement by femtosecond spectral interferometry for applications in spectroscopy," *J. Opt. Soc. Am. B*, vol. 12, pp. 2467-74, (1995), which is incorporated herein by reference. Advantageously, the instrument may be configured in embodiments that require neither sample rotation nor reference reflectors. The physical apparatus is suitable for integration with high numerical aperture (NA) confocal microscope systems. Data acquisition in accordance with the invention is robust because spectral interferograms are acquired in snapshots, one per voxel, while the sample is translated in three dimensions. Because the instrument acquires all the data needed at a given sample position in a single spectral interferogram snapshot, the method is insensitive to vibrations and source intensity noise. The instrument may advantageously measure the complex group refractive index, which includes both a real component indicating the wavelength derivative of the phase retardance at a given sample location, as well as an imaginary part indicating the absorption.

Derivation of a Refractive Index Reconstruction Relation.

One embodiment of an instrument is now described with reference to FIG. 1. In accordance with the embodiment depicted, a transmission confocal microscope 100 is embedded in one arm of a Mach-Zehnder interferometer. Incident on the interferometer is light from a broadband source of illumination 102, such as a mode-locked laser or a superluminescent diode. Monochromatic illumination is not sufficient to infer the group refractive index, which inherently involves the propagation of polychromatic light. This illumination is divided by a beamsplitter 104 into a reference beam 106 and a sample beam 110. The sample beam is focused by an illumination microscope objective 112 into the object space V, where the sample under test (also referred to herein as object, not shown) is movably positioned at a focus F of the microscope objective. A second objective 114, confocal with the first, collects the illumination beam and recollimates it. The reference beam 106 is adjusted so that the total delay through the reference arm is slightly less than that through the sample arm. A second beamsplitter 120 interferes the sample and reference beams by recombining them into a beam 124, and the recombined beam 124 is focused into a confocal pinhole 130 with a focussing element 134. The recombined beam is further recollimated from this pinhole by a collimating element 140, and the spectrum of light passing through the pinhole is sampled by means of spectral interferometry (that utilizes, e.g., a phase-detection member dividing the incoming light into a multiplicity of images and comparing them). In some embodiments, a grating spectrometer can be used. The pinhole 130, together with the elements 134 and 140 that form the relay optics, act as a spatial, telecentric in both object and image spaces, low-pass filter and selects substantially the lowest spatial mode of the recombined beam 124. The data acquisition consists of translating, in three dimensions, the sample with respect to the focus F of the microscope objective 112 so as to have the successive volume elements of the sample illuminated with the illuminating beam 110, and acquiring successive spectral interferograms, produced by recombined beam 124, that correspond to illumination of successive volume elements of the sample. In some embodiments, illumination of successive volume elements within the sample may be alternatively achieved by synchronously translating the first and the second confocal microscope objectives with respect to the sample. For the purposes of the disclosure and appended claims, positioning of a confocal microscope within an arm of an interferometer is referred to as interferometric configuring of the microscope. It is to be understood that various other interferometric configurations, such as Michelson, Sagnac, and single-path interferometers, where the reference and sample beams propagate along the same path, are within the scope of the present invention.

Derivation of a refractive-index-reconstructive relation is now described in three sections. In a first section, the field at the pinhole is computed for a single frequency focused illumination beam scattered from the sample. This is used to find the relationship between the three dimensional Fourier components of the object refractive index at a single illumination frequency and the measured field at the pinhole. In the next section, the derivation is extended to multiple illumination frequencies, which allows to compute the group refractive index. Finally, a solution is found to the inverse scattering problem to allow reconstruction of the group refractive index from measurements of the spectral interferograms (also referred to herein as interferometric images).

To find the field scattered to the pinhole by the sample, we consider the field u(r) in the object space V. The field satisfies the inhomogeneous reduced wave equation:

$$\nabla^2 u(r) + k^2 [n_0(r) + \in n(r-r_0)]^2 u(r) = 0 \quad (1)$$

where k is the free-space wave number of the field, $n_0(r)$ is the refractive index representing the optical system of FIG. 1 without an object, and n(r) is the inhomogeneous refractive index of the object. The inhomogeneous refractive index n(r) is treated as a perturbation of order of a small parameter $\in$. The inhomogeneity n(r) is zero outside of the volume V. We make the first Rytov approximation, where the field $u(r) = u_0(r) \exp[\in \phi(r)]$, where $u_0(r)$ obeys the unperturbed wave equation $\nabla^2 u_0 + k^2 n_0^2 u_0 = 0$ and $\phi$ is a complex phase. The first Rytov approximation is described in Born & Wolf, *Principles of Optics*, Sec. 13.5, (7th ed., 1999), pp. 726 ff which is incorporated herein by reference. To first order in $\in$, the solution for $\phi$ is, then, $$u_0(r;k)\phi(r,r_0;k) = -2k^2 \int_V d^3 r' g(r,r';k) u_0(r';k) n_0(r') n(r'-r_0) \quad (2)$$

where g(r,r';k) is the Green's function which is the solution to the unperturbed wave equation $\nabla^2 g + k^2 n_0 g = -4\pi\delta(r'-r)$. In the absence of an object, the refractive index in the volume V is $n_0(r) = n_b$. The illumination beam in V has a field denoted by $u_0(r;k)$. The field is given in terms of its Fourier spectrum at the beam waist plane z=0:

$$u_0(r';k) = (2\pi)^{-2} k^{-2} \int_V d^2 q' \exp[i(q' \cdot r') + k_z(q')z'] \tilde{B}\left(\frac{q'}{k}\right) \quad (3)$$

where $$\tilde{B}\left(\frac{q'}{k}\right)$$

is the Fourier expansion of the beam field in the plane z=0, and $k_z(q') = \sqrt{k^2 n_b^2 - q'^2}$. The scaling and normalization with k ensures that the beam amplitude at the focus is the same for all frequencies k. For a Gaussian beam, $$\tilde{B}\left(\frac{q'}{k}\right) = B_0 \exp(-q'^2 \alpha^2 / 2k^2),$$

where $\alpha = \pi/NA$, and NA is the numerical aperture of the focusing lens 112.

Next, we determine the Green's function g(r,r';k). In the volume V, the field is relayed to the pinhole plane P by the "exit imaging optics" 144 shown in FIG. 1. These optics may comprise a lens 114 recollimating the sample-illuminating beam and a lens 134 refocusing the combined beam 124 through the pinhole 130. For simplicity, these imaging optics 144 are designed to afocally and telecentrically image the plane z=0 in V to the plane of the pinhole. The propagation of the field through the exit imaging optics 144 can then be described by a space-invariant point-spread-function $$P(r'';k) = (2\pi)^{-2} \int d^2 q'' \exp[-i(q'' \cdot r'') + k_z(q')z'] \tilde{P}\left(\frac{q'}{k}\right),$$

where the angular spectrum $$\tilde{P}\left(\frac{q'}{k}\right)$$

is the coherent transfer function of the exit optics. The total Green's function $g(r,r';k)$ which describes the propagation of light 124 to the pinhole plane P is $$g(r, r'; k) = \frac{ik}{2\pi} \int_{z''=0} d^2 r'' P(r - r''; k) \qquad (4)$$

$$\int d^2 q k_z(q)^{-1} \exp[-i(q'' \cdot (r'' - r') + k_z(q')(z'' - z))]$$

using the Weyl expansion of a spherical wave as plane waves. This can be simplified by inserting the definition of $P(r;k)$:

$$g(r, r'; k) = \frac{ik}{(2\pi)^3} \int_{z''=0} d^2 r'' \int d^2 q'' \exp[-i(q'' \cdot r - r'')] \tilde{P}\left(\frac{q'}{k}\right) \qquad (5)$$

$$\int d^2 q k_z(q)^{-1} \exp[-i(q'' \cdot (r'' - r') + k_z(q')(z'' - z))]$$

Switching the order of the integrations, the integration over r'' yields $(2\pi)^2 \delta^{(2)}(q''+q)$. Further integration over q'' yields $$g(r, r'; k) = \qquad (6)$$

$$\frac{ik}{2\pi} \int d^2 q k_z(q)^{-1} \tilde{P}\left(-\frac{q}{k}\right) \exp[i(q \cdot (r - r') - k_z(q')z')]$$

Next, the complex phase of the scattered field at the pinhole plane is determined. Substituting Eqs (3) and (6) into Eq. (2) yields $$u_0(r; k)\phi(r, r_0; k) = \qquad (7)$$

$$-2ik(2\pi)^{-3} \int_V d^3 r' n_0(r') n(r' - r_0) \int d^2 q' \exp[i(q' \cdot r') + k_z(q')z']$$

$$\tilde{B}\left(\frac{q'}{k}\right) \int d^2 q k_z(q)^{-1} \tilde{P}\left(-\frac{q}{k}\right) \exp[i(q \cdot (r - r') - k_z(q')z')]$$

The pinhole 130 (shown in FIG. 1) is placed so its center is at position r=0 on the pinhole plane P. We assume that the pinhole is small enough so that the value of $\phi(r,r_0;k)$ at r=0 is similar to its value over the entire pinhole. In this case, we concern ourselves only with the value $\phi(0, r_0;k)$. We define the Fourier transform $\tilde{\phi}(Q;k) = \int d^3 r_0 \exp[iQ \cdot r_0] \phi(0, r_0;k) \phi(Q;k) = \int d^3 r_0 \exp[iQ \cdot r_0] \phi(0,r_0;k)$, and substitute it into Eq. (7):

$$u_0(0; k)\tilde{\phi}(Q; k) = -2ik(2\pi)^{-3} \int d^3 r_0 \int d^3 r' n_0(r') n(r' - r_0) \qquad (8)$$

$$\exp[iQ \cdot r_0] \int d^2 q' \exp[i(q' \cdot r') + k_z(q')z'] \tilde{B}\left(\frac{q'}{k}\right)$$

-continued $$\int d^2 q k_z(q)^{-1} \tilde{P}\left(-\frac{q}{k}\right) \exp[i(q \cdot (r - r') - k_z(q')z')]$$

Switching the order of integration and performing the integral over $r_0$, we can identify the Fourier transform of n(r):

$$u_0(0; k)\tilde{\phi}(Q; k) = -2ik(2\pi)^{-3} \tilde{n}(Q) \int d^2 q' \tilde{B}\left(\frac{q'}{k}\right) \qquad (9)$$

$$\int d^2 q k_z(q)^{-1} \tilde{P}\left(-\frac{q}{k}\right) \int_V d^2 r'_p dz' n_0(r') \exp[i(Q_P \cdot r_P + Q_z z)']$$

$$\exp[i(q' r'_P + k_z(q')z)'] \exp[i(-q \cdot r'_p - k_z(q')z')]$$

where $z'=r' \cdot \hat{z}, r_P'=r'-z'\hat{z}, Q_z=Q \cdot \hat{z}$ and $Q_P=Q-\hat{z}Q_z$. In the volume V, without an object, the refractive index is a constant value $n_b$, so that $n_0(r)=n_b$ in V. The integral over $r_P'$ can then be integrated to be a two-dimensional delta function:

$$u_0(0; k)\tilde{\phi}(Q; k) = \qquad (10)$$

$$-2ikn_b(2\pi)^{-1} \tilde{n} \int d^2 q' \tilde{B}\left(\frac{q'}{k}\right) \int d^2 q k_z(q)^{-1} \tilde{P}\left(-\frac{q'}{k}\right) \int_V dz'$$

$$\delta^{(2)}(Q_P + q' - q) \exp[iQ_z z'] \exp[ik_z(q')z'] \exp[-ik_z(q)z']$$

Performing the integration over q' yields $$u_0(0; k)\tilde{\phi}(Q; k) = -2ikn_b(2\pi)^{-1} \tilde{n}(Q) \int d^2 q k_z(q)^{-1} \tilde{P}\left(-\frac{q}{k}\right) \tilde{B}\left(\frac{q - Q_P}{k}\right) \qquad (11)$$

$$\int_V dz' \exp[iQ_z z'] \exp[ik_z(q - Q_P)z'] \exp[-ik_z(q)z']$$

Performing the integration over z' yields a one-dimensional delta function:

$$u_0(0; k)\tilde{\phi}(Q; k) = -2ikn_b \tilde{n}(Q) \int d^2 q k_z(q)^{-1} \tilde{P}\left(-\frac{q}{k}\right) \qquad (12)$$

$$\tilde{B}\left(\frac{q - Q_P}{k}\right) \delta[Q_z + k_z(q - Q_P) - k_z(q)]$$

For brevity, one can define a three-dimensional transfer function of the instrument by $$\tilde{F}(Q; k) = \qquad (13)$$

$$-2in_b \int d^2 q k_z(q)^{-1} \tilde{P}\left(-\frac{q}{k}\right) \tilde{B}\left(\frac{q - Q_P}{k}\right) \delta[Q_z + k_z(q - Q_P) - k_z(q)]$$

so that $u_0(0;k)\tilde{\phi}(Q;k)=k\tilde{n}(Q)\tilde{F}(Q;k)$

The complex phase $\phi$ is then the 3-D convolution of the index profile n(r) and a three-dimensional point spread function. (The Mathematical Note below presents a version of Eq. (13) suitable for numerical integration.) However, $\phi$ cannot be measured directly. Rather, we measure the intensity at the pinhole of the interference between the reference and sample signals, and infer the sample field at the pinhole, and, from this, the complex phase. Given the definition of the complex phase, the sample field at the pinhole will be $u_s=u_0(0;k)\exp[\phi(0,r_0;k)]$. The reference optical field at the pinhole 130, corresponding to a contribution of the reference beam 106 to the recombined beam 124, is delayed by a time $\tau$ relative to the sample field, corresponding to a contribution, to the beam 124, of the sample beam 110 that has assed through the object. Therefore, the reference filed at the pinhole 130 is given by $u_r$ exp($ikc\tau$) where c is the speed of light. The total field at the pinhole is $$I(r_0;k,\tau)=|u_r\exp(ikc\tau)+u_0(0;k)\exp[\phi(0,r_0;k)]|^2 \quad (14)$$

By performing phase-shifting and measuring $I(r_0;k,\tau)$ for three values of $\tau$ such that $kc\tau=0$, $\pi/2$, and $\pi$, the complex phase can be found $$\phi(0, r_0; k) = \quad (15)$$

$$\log\left\{(u_r^* u_0(0; k))^{-1}\left[\frac{1-i}{4}I(r_0; k, 0) - \frac{1+i}{4}I(r_0; k, \pi/ck) + \frac{i}{2}I(r_0; k, \pi/2ck)\right]\right\}$$

The logarithm operator used in Eq. (15) is the complex logarithm, which is multiple-valued due to ambiguity arising from the ambiguity of the complex phase value arising from multiples of $2\pi$. Because of this ambiguity, phase unwrapping needs to be performed on $\phi(0, r_0;k)$. Estimating the complex phase may be can be problematic if there are values of Re{$\phi(0, r_0;k)$} that are well below zero, i.e., if absorption in the sample is so great that little optical power is transmitted through the sample. At those positions, and/or wavelengths, the phase (the imaginary part of $\phi$) is poorly estimated at these points. These points are accordingly less weighted in subsequent calculations.

Group Refractive Index Measurement.

In practice, the imaginary part of $\phi$ may be difficult to measure because it depends sensitively on changes, of the total optical path length through the interferometer, that are only on the order of a wavelength. Rather, one can use the phase difference between different illumination frequencies to estimate the group refractive index. Upon differentiation of $u_0\tilde\phi$ with respect to k, we find $$\frac{d(u_0\tilde\phi)}{dk} = \tilde{n}\tilde{F} + k\frac{d\tilde{n}}{dk}\tilde{F} + k\tilde{n}\frac{d\tilde{F}}{dk} \quad (16)$$

We now assume that $$\frac{d\tilde{F}}{dk}$$

has little wavelength dependence, so that $$\frac{d\tilde{F}}{dk} \approx 0.$$

The function $\tilde{F}$ is dependent on the beam spectrum $\tilde{B}$ and aperture spectrum $\tilde{P}$. For the purpose of minimizing $$\left|\frac{d\tilde{F}}{dk}\right|,$$

the aperture functions $\tilde{B}$ and $\tilde{P}$ are considered to be achromatic. For focused beams where all frequencies have the same numerical aperture, the primary difference between the beams is the spot sizes at the focus, which scale with $k^{-1}$. For a small fractional bandwidth $$\frac{\Delta k}{k}$$

of illumination (e.g. 10-20%) the contribution due to $$\frac{d\tilde{F}}{dk}$$

will be small. By neglecting $$\frac{d\tilde{F}}{dk}$$

it is found that $$\frac{d(u_0\tilde\phi)}{dk} = \tilde{F}(Q;k)\left[\tilde{n} + k\frac{d\tilde{n}}{dk}\right] = \tilde{F}(Q;k)\tilde{n}_g(Q) \quad (17)$$

In Eq. (17), the group refractive index is the term $$\tilde{n}_g = \tilde{n} + k\frac{d\tilde{n}}{dk}.$$

This indicates that $$\frac{d(u_0\phi)}{dk}$$

is the 3-D convolution of the group refractive index of the object and the 3-D point spread function of the beam. Therefore, deconvolution of $$\frac{d(u_0\phi)}{dk}$$

can be used to estimate the three-dimensional distribution of the group refractive index of the object. Because $$\frac{d(u_0\phi)}{dk}$$

is made with a differential measurement between samples of $\phi$ at two or more frequencies k, it does not depend on the absolute phase delay through the object and therefore is easier to measure. The imaginary part of $$\frac{d\phi}{dk}$$

is the differential group optical path length between the reference and sample arms.

To obtain a measure of frequency-dependent complex phase of light that has traversed the sample, one can use a phase-detection member comprising a spectrometer (such as a grating spectrometer in FIG. 1) that spectrally resolves interferometric images by measuring the spectrum of the interferometric signal passing through the pinhole. Spectral interferometry enables the interferometric cross-correlation of the reference and sample beams to be inferred from the measured spectrum. The intensity measured at a particular frequency in the spectrometer (indicated in Eq. (14)) can be divided into three components, the spectrum of the reference alone, the spectrum of the signal passing through the sample alone, and the interference component between the reference and object signals:

$$I(r_0;k,\tau)=|u_r|^2+\phi|u_0(0;k)\exp[\phi(0,r_0;k)]|^2+2Re\{u_r{}^*u_0(0;k)\exp[\phi(0,r_0;k)-ikc\tau]\} \quad (18)$$

Phase-shifting can be used to distinguish the interference component. In an alternative embodiment, if the reference signal precedes the sample signal sufficiently in time that the two do not overlap, the Hilbert transform can be used to compute the complex analytic signal of the interferogram, which contains the phase and amplitude of $u_r/u_0(0;k)$.

The optical field scattered by the object is expressed as $u_s(0,r_0;k)=u_0(0;k)\exp[\phi(0,r_0;k)]$. To compute the complex phase $\phi$ from the scattered optical field, the logarithm function must be used, which results in a phase ambiguity of $2\pi$. Fortunately, the phase wrapping problem can be avoided because $$\frac{d(u_0\phi)}{dk}$$

is needed to measure the group refractive index is, not $\phi$ itself. For brevity, define $$u_0\phi' = \frac{d(u_0\phi)}{dk},$$

which is given by $$u_0\phi' = \frac{d(u_0\phi)}{dk} = u_0\frac{d\phi}{dk} + \frac{du_0}{dk}\phi. \quad (19)$$

To simplify Eq. (19), we now examine Eq. (3) with the condition r'=0, the position of the pinhole. As defined, the amplitudes of all of beams at frequencies k are the same at their respective foci. Because the exit imaging optics are achromatic, the same will be true at the pinhole. Therefore $$\frac{du_0}{dk} = 0,$$

and $$\phi' = \frac{d\phi}{dk}.$$

Using this fact, a finite-difference approximation from two samples of the field $u_s$ at frequencies k and k+$\Delta$k can be found:

$$\phi' = \frac{d\phi}{dk} \approx \frac{\phi(0, r_0; k + \Delta k) - \phi(0, r_0; k)}{\Delta k} = \qquad (20)$$

$$\frac{\log\frac{u_s(0, r_0; k + \Delta k)}{u_0(0; k + \Delta k)} - \log\frac{u_s(0, r_0; k)}{u_0(0; k)}}{\Delta k} =$$

$$\frac{1}{\Delta k}\log\frac{u_s(0, r_0; k + \Delta k)}{u_s(0, r_0; k)}\frac{u_0(0; k)}{u_0(0; k + \Delta k)} = \frac{1}{\Delta k}\log\frac{u_s(0, r_0; k + \Delta k)}{u_s(0, r_0; k)}$$

If instead of sampling $u_s$ at just two frequencies, the field $u_s$ is sampled at N frequencies $k_i$ where $1 \leq i \leq N$, as would occur for a spectrometer sampling an entire interferometric spectrum. An estimate of the average $\phi'$ over the interval $k_1$ to $k_N$ can be calculated using $$\phi' = \sum_{i=1}^{N-1} \frac{1}{k_{i+1} - k_i}\log\frac{u_s(0, r_0; k_{i+1})}{u_s(0, r_0; k_i)} \qquad (21)$$

Because the phases between the samples of $u_s$ are subtracted by the division operation before the logarithm is taken, phase wrapping is not necessary to compute $\phi'$. The complex logarithm need only be applied on the principal branch with imaginary part between $-i\pi$ and $i\pi$. Limiting the logarithm to this branch effectively requires that the phase differences between adjacent samples of $u_s$ are less than $\pi$ and greater than $-\pi$. As an alternative estimation method for $\phi'$, the samples of phase can be weighted by their magnitudes so that phase differences that correspond to samples with greater spectral magnitude contribute more to the complex phase estimate:

$$\phi' = \frac{\sum_{i=1}^{N-1}\frac{|u_s(0, r_0; k_{i+1})u_s(0, r_0; k_i)|}{k_{i+1} - k_i}\log\frac{u_s(0, r_0; k_{i+1})}{u_s(0, r_0; k_i)}}{\sum_{i=1}^{N-1}|u_s(0, r_0; k_{i+1})u_s(0, r_0; k_i)|} \qquad (21b)$$

Because a spectrometer can capture the data needed to compute an estimate of $\phi'$ without requiring phase shifting or phase unwrapping, this method is a robust and sensitive way to measure the group refractive index of a sample with diffraction-limited resolution in three dimensions. The sample must simply be translated in three-dimensions while the spectrum of the field at the pinhole is sampled. Using the Hilbert transform to infer the phase of the interferogram avoids phase shifting, and the fact that only phase differences are needed avoids the phase unwrapping requirement, which simplifies the apparatus and minimizes error.

Linear Solutions to the Inverse Problem for Group Refractive Index.

Eq. (17) expresses a relationship between the group refractive index of an object and the complex phase of a beam passing through the object. In the spatial domain, this relationship is a three-dimensional convolution of the group refractive index with a point spread function:

$$u_0' = u_0(0;k)\phi'(0;r_0;k) = Fn_g = \int_V d^3 n_g(r)F(r_0-r;k) \quad (22)$$

$$F(r;k) = (2\pi)^{-3}\int d^3Q\exp(-ir\cdot Q)\tilde{F}(Q;k)$$

$$n_g(r) = (2\pi)^{-3}\int d^3Q\exp(-ir\cdot Q)\tilde{n}_g(Q;k)$$

The operator equation $u_0'=Fn_g$ implicitly defines the operator F in terms of the 3-D convolution of the kernel F(r;k) with the refractive index function $n_g(r)$ as shown in Eq. (22). With this specification of the forward problem, we can pose the inverse problem as the minimization of a squared error functional:

$$n_g^+ = \operatorname*{argmin}_{n_g}|u_0'-Fn_g|^2 + \gamma|n_g|^2 = \operatorname*{argmin}_{n_g}\int_V d^3r_0\left|u_0(0;k)\phi'(r_0;k) - \int_V d^3 r n_g(r)F(r_0-r;k)\right|^2 + \gamma\int_V d^3 r|n_g(r)|^2 \quad (23)$$

The term proportional to γ is included to effect Tikhonov regularization to stabilize the solution. Formally, the solution is given by the Tikhonov-regularized pseudoinverse solution $n_g^+=(F\dagger F+\gamma I)^{-1}F\dagger u_0'$. Because the operation of F on a function $u_0'$ is a 3-D convolution, it is easier to express the pseudoinverse in the frequency domain:

$$\tilde{n}_g^+(Q;k) = \frac{u_0(0;k)\tilde{\phi}'(Q;k)\tilde{F}^*(Q;k)}{|\tilde{F}(Q;k)|^2 + \gamma} \quad (24)$$

However, the space-invariant filter of Eq. (24), while simple to implement, suffers from a deficiency. Because the calculated phase difference φ' is given by a logarithmic relationship to $u_s$ by Eq. (20), a constant error variance in the measurement of $u_s$ does not necessarily produce a constant error variance in φ'. Given the differential relation $$\phi' = \frac{du_s}{dk}\bigg/u_s,$$

it is clear that smaller $|u_s|$ will produce a larger error in φ'. It is desirable to modify the solution to account for the error in individual measurements of φ'. We define an alternate least-squares minimization that weights the error according to the confidence in various samples of φ':

$$n_g^+ = \operatorname*{argmin}_{n_g}|W(u_0'-Fn_g)|^2 + \gamma|n_g|^2 = \quad (25)$$

$$\operatorname*{argmin}_{n_g}\int_V d^3 r_0|W(r_0;k)|^2\bigg|u_0(0;k)\phi'(r_0;k) - \int_V d^3 r n_g(r)F(r_0-r;k)\bigg|^2 + \gamma\int_V d^3 r|n_g(r)|^2$$

This expression defines a weighting operator W in the spatial domain V with a corresponding weighting function $W(r_0)$, which is assigned greater weights to values of φ'(0;$r_0$;k) for which there is greater certainty. The weighting function that properly accounts for the confidence in φ' given a constant error variance for $u_s$ is $W(r_0)=\exp[\operatorname{Re}\phi'(0;r_0;k)]$. The weighted Tikhonov-regularized formal solution is $n_g^+=(F\dagger W\dagger WF+\gamma I)^{-1}F\dagger W\dagger Wu_0'$. Because weighting is performed in the spatial domain, the solution can no longer be computed using a space-invariant filter. However, the operators W and F are diagonal in their respective domains, so the numerical solution of the problem lends itself well to sparse matrix methods such as the preconditioned conjugate gradient method.

Simulation and Discussion of the Methods Described Above.

Figure 2:
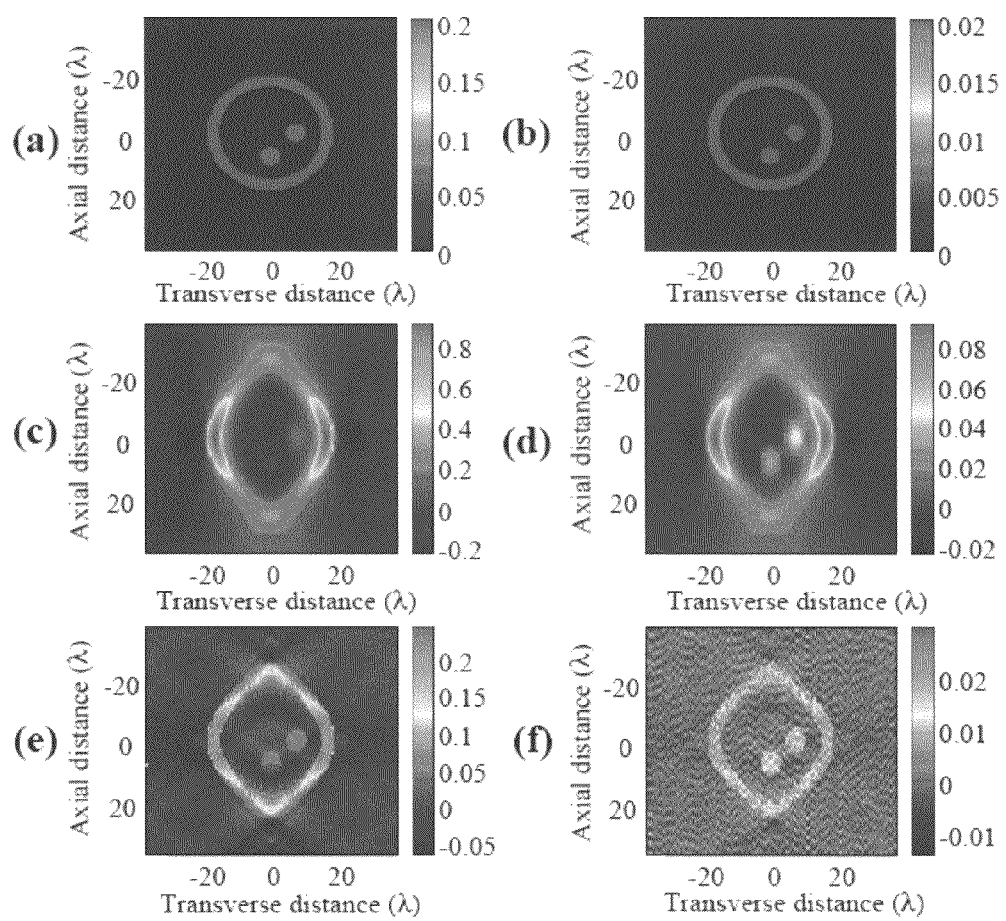
FIG. 2 plots several parameters as a function of beam position in an identical cross-section of a simulated object: (a) the real part of the refractive index, (b) the imaginary part of the refractive index, (c) total optical delay between two measured frequencies acquired by the confocal microscope (in radians), (d) total attenuation difference between two measured frequencies (in nats), (e) the real part of the weighted least-squares reconstruction of the index profile, and (f) the imaginary part of the weighted least-squares reconstruction of the index profile.

The feasibility, resolution, and noise resilience of measuring group refractive index with the embodiments of a method described above has been demonstrated with a simulation, where a simulated object is a refracting and absorbing spherical shell with spherical inclusions intended to be a simple phantom evocative of cells with their constituent organelles. The simulated volume is 75λ×75λ×75λ in size sampled every λ/2, where λ is the center wavelength of the illumination. The shell is 35λ is diameter, and 3λ thick. The background refractive index is 1.0, and all of the refractive indices of the simulation scale with this index (e.g. if the background index was 1.33 all of the reconstructed indices would likewise be multiplied by 1.33). The inclusions are also spheres 3λ in diameter. The distribution of the refractive index is as follows: the shell has a refractive index of 1.2+0.02 i, and each of the inclusions has a refractive index of 1.06+0.02 i. FIGS. 2(a) and 2(b) illustrate a slice through such simulated synthetic object, showing the real and imaginary parts of the refractive index of the object, respectively.

Figure 3:
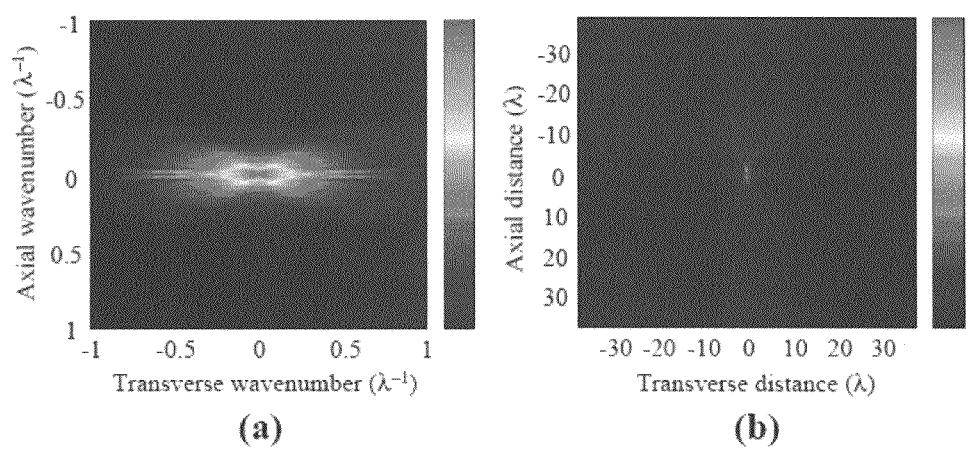
FIG. 3 depicts two-dimensional density plots of: (a) a three-dimensional transfer function, $\tilde{F}(Q;k)$, and (b) a three-dimensional point-spread function, of the simulated confocal microscope. Both functions are radially symmetric about the $Q_1=0$ axis.

The simulated optical system has a two numerical apertures associated with it: the numerical aperture of the illumination beam optics, and the numerical aperture of the relay optics to the pinhole. In our simulation, they were both set to have a numerical aperture (NA) of 0.75. In other specific embodiments of the invention, the value of NA may be chosen in excess of 0.75 to obtain better spatial resolution. The functions $$\tilde{B}\left(\frac{q'}{k}\right) = 1$$

and $$\tilde{P}\left(\frac{q'}{k}\right) = 1$$

for |q'|<(NA)k and zero otherwise. Using these functions, the 3-D transfer function $\tilde{F}(Q;k)$ was calculated using Eq. (28) and numerical integration. A 2-D projection of the 3-D function $\tilde{F}(Q;k)$ is shown in FIG. 3(a), which shows the bandpass of the optical system in terms of the transverse and axial spatial frequencies as a fraction of k, the illumination wave number. Because this simulation is of scalar fields, the 3-D point frequency response is rotationally symmetric about $|Q_P|=0$. The 2-D projection of the 3-D point spread function, which is the inverse 3-D Fourier transform of $\tilde{F}(Q;k)$, is shown in FIG. 3(b). This shows the axial and transverse resolution of the system in units of λ, and is likewise rotationally symmetric.

Using the organelles phantom and calculated frequency response of the system, the synthetic interferometric data were computed. To do this, first the complex phase $\phi'(0;r_0;k)$ was calculated at frequencies k and k+Δk using the 3-D convolution of the refractive index profile with the 3-D impulse response as in Eq. (13). In the simulation, Δk=0.03 k, so that the group delay is being measured from a 3% fractional bandwidth. In alternative embodiments, fractional bandwidth may be chosen to be at least 2 percent. The field $u_s=u_0(0;k)\exp[\phi(0,r_0;k)]$ was calculated at the two frequencies, and from this the intensity of the interferometric measurements $I(r_0;k,\tau)$ could be calculated using Eq. (18) for τ=0, π/2, and π. Noise was added to the measured intensity to achieve a signal-to-noise ratio of 20 dB. FIGS. 2(c) and 2(d) describe the synthetic data $\phi'\Delta k$ iand show, respectively, the difference in retardance and attenuation between the frequencies k and k+Δk measured at each position of the focus F of the illuminating beam across the sample. The total retardance difference between the two frequencies in FIG. 2(c) is given in radians, and corresponds to the real part of $\phi'\Delta k$. The total attenuation difference between the two frequencies in FIG. 2(d) is given in nats (also called nepers), and corresponds to the imaginary part of $\phi'\Delta k$.

Using the synthetic data, which consisted of interferometric intensity samples measured at two frequencies k and k+Δk and three different τ over $r_0$, the inverse scattering process was performed as follows:

From the intensity samples, estimates of φ were computed with Eq. (15).

From φ, estimates of $u_s$ were computed using $u_s=u_0 \exp \phi$.

With φ and $u_s$, an estimate of $\phi'$ was calculated with Eq. (20).

The weighting function was calculated using $W(r_0)=\exp[Re\phi'(0;r_0;k]$, which assigns larger weights to estimates of $\phi'$ for which more power from the sample arm was detected at the pinhole.

The weighted least squares solution of Eq. (25) for $n_g^+$ was computed using the preconditioned conjugate gradient method. The system solved was formally $(F\dagger W\dagger WF+\gamma I)n_g^+=F\dagger W\dagger Wu_0'$. The preconditioner was the unweighted inverse solution, given by the space-invariant operator $(F\dagger F+\gamma I)^{-1}$.

The result of the inversion is shown in the refractive index reconstruction of FIGS. 2(e) and 2(f). FIG. 2(e) illustrates the reconstructed real part of the refractive index, and FIG. 2(f) illustrates that the imaginary part. Because of the finite numerical aperture and frequency space coverage of the instrument, it is clear that the reconstructed object has been elongated in the axial direction. This elongation is consistent with the depth-of-field of a typical microscope with the simulated numerical aperture. On the boundaries of the outer sphere parallel to the axial direction, there was less elongation and the estimate of the refractive index is more accurate. In addition, the estimated refractive index of the inclusions is also elongated, but remains similar to the phantom. While the simulation does not show a perfectly reconstructed refractive index distribution of the object, it depicts the limitations that an actual instrument would have, which illuminates an object with a finite numerical aperture beam from a single direction.

A rough estimate of the magnitude of the noise in the refractive index reconstruction can be computed. In general, the refractive index variation Δn will depend on the numerical aperture NA, the fractional bandwidth of the source $$\frac{\Delta k}{k},$$

and the signal to noise ratio SNR in the measurements of the optical fields. Tighter focusing the sample beam 108 would provide better resolution, but at expense of less retardation at the focus due to decrease of the depth-of-focus within volume V. More bandwidth would produce a larger difference in retardance at the extrema of the source spectrum. Finally, higher SNR would allow one to better distinguish small phase variations, with the minimum detectable phase difference being approximately $(SNR)^{-1}$ in radians. Accounting for these factors, we estimate that $$\Delta n = \frac{n_b k (NA)^2}{2\pi \Delta k (SNR)}.$$

For the simulation, Δn≈0.03, which is consistent with the optical field noise seen in FIGS. 2(e) and 2(f).

In addition, the simulation shows that if the illumination is limited to one direction unavoidable blurring in the axial direction can be expected. This is a limitation of any confocal microscope. This limitation can be mitigated—and, therefore, the spatial resolution of imaging an object with a confocal microscope can be improved—by imaging the object from multiple illumination angles (or, from multiple viewpoints) rather than fixing the orientation of the illumination beam relative to the object. In practice, axial resolution on the order of a few wavelengths (for the sample illuminated with infrared, such as near-infrared, or visible light) provides μm-scale resolution which is adequate for many applications.

The embodiments of a microscope and a method for measuring group refractive index of a medium described in accordance with the present invention allow for investigation of the microscopic variations of a refractive index of an object. The robustness of the embodiments derives from the fact that they require only relative phase and amplitude measurements between two or more wavelengths transmitted through the object. Relative measurements are less error prone than absolute measurements of the total phase retardance and attenuation, especially because the interference measurements at different frequencies can be captured simultaneously with an array spectrometer.

Mathematical Note.

Eq. (13) for $\tilde{F}(Q;k)$ is a two-dimensional integral with a one-dimensional delta function, which we simplify into a one-dimensional integral. We change variables to $$s = \frac{Q_P}{2} - q,$$

define $\cos \theta = (Q_P \cdot s)/Q_P s$, and rewrite the integral as $$\tilde{F}(Q;k) = -2in_b \int_{-\pi/2}^{\pi/2} d\theta s k_z(q)^{-1} \tilde{P}\left(-\frac{q}{k}\right) B\left(\frac{q-Q_P}{k}\right) \delta[f(s)] \quad (26)$$

where $f(s) = Q_z + \sqrt{k^2 + \left(\frac{Q_P}{2}\right)^2 - s^2 - Q_P s \cos\theta} - $ $$\sqrt{k^2 - \left(\frac{Q_P}{2}\right)^2 - s^2 + Q_P s \cos\theta}$$

In the inner integral, the delta function selects the values such that f(s)=0 which are $$s = \pm \frac{Q_z \sqrt{4k^2 - Q_P^2 - Q_z^2}}{2\sqrt{Q_z^2 + Q_P^2 \cos^2\theta}}. \quad (27)$$

Because the integration bounds on s are for nonnegative s, only the positive root need be considered. Using the sifting theorem, Eq. (26) integrates to $$\tilde{F}(Q;k) = -2in_b \int_{-\pi/2}^{\pi/2} ds s k_z(q)^{-1} \tilde{P}\left(-\frac{q}{k}\right) B\left(\frac{q-Q_P}{k}\right) \left|\frac{df}{ds}\right|^{-1} \quad (28)$$

$$s = \frac{|Q_z|\sqrt{4k^2 - Q_P^2 - Q_z^2}}{2\sqrt{Q_z^2 + Q_P^2 \cos^2\theta}}$$

$$q = \frac{Q_P}{2} - \frac{Q_P}{Q_P} s \cos\theta - \frac{Q_\perp}{Q_\perp} s \sin\theta, \; Q_\perp \cdot \{Q_P, \hat{z}\} = 0$$

$$\frac{df}{ds} =$$

$$\frac{2s - Q_P \cos\theta}{2\sqrt{k^2 - \left(\frac{Q_P}{2}\right)^2 - s^2 + Q_P s \cos\theta}} - \frac{2s + Q_P \cos\theta}{2\sqrt{k^2 - \left(\frac{Q_P}{2}\right)^2 - s^2 - Q_P s \cos\theta}}$$

This formula can be numerically integrated to calculate $\tilde{F}(Q;k)$.

Relationship Between Group Refractive Index Confocal Microscopy and Projection Index Computed Tomography.

An alternative method for measuring the group refractive index of an object is projection index computed tomography (PICT). Group refractive index confocal microscopy measures the group delay of the focused beam passing through the object as the object is translated in three-dimensions. PICT illuminates the object with low numerical aperture pencil-like beams from many directions and samples the transit time of the beams through the sample for many lateral displacements and rotations of the sample. PICT measures parallel projections of the group refractive index in a manner analogous to the sampling of X-ray attenuation by X-ray computed tomography (CT). A deficiency of PICT is that a low numerical aperture beam must be used so that the illumination beams are sufficiently similar to the parallel projections used in CT. Confocal microscopy, on the other hand, suffers from the problem that the resolution is typically poorer in the axial direction than in the transverse directions. Ideally, an imaging modality could achieve high resolution in all three dimensions.

In embodiments of the invention, this deficiency of confocal microscopy may be overcome by illuminating the object from multiple viewpoints and sampling the group delay as the object is translated. Observations of the object from multiple view angles using confocal microscopy can compensate for the axial blurring. We devise a method by which the observations of an object from multiple viewpoints using confocal microscopy can be combined into a single estimate of the three-dimensional refractive index of an object.

According to one embodiment of the invention, rather than observing the object using only one viewpoint—as, e.g., in FIG. 1 where the object (not shown) is scanned by the beam 110 that propagates along the z-direction—we observe the object from $N_V$ viewpoints. For each of these viewpoints, there is a proper (non-reflecting) three-dimensional rotation matrix $R_i$ such that $R_i^\dagger R_i = I$ for $1 \leq i \leq N_V$. The rotation matrices describe the relationship between a fixed coordinate system and the coordinate system the object is rotated to when sampling each set of confocal projections. For example, for a rotation in the x-z plane, the rotation matrices are given by $$R_i = \begin{pmatrix} \cos\theta_i & 0 & \sin\theta_i \\ 0 & 1 & 0 \\ -\sin\theta_i & 0 & \cos\theta_i \end{pmatrix} \quad (29)$$

where $\theta_i$ are the angles of the rotations. The measurements of $\phi'$ from each of these viewpoints is given by $\phi_i'(R_i^\dagger r_0; k)$. Using these data, the least squares-solution of Eq. 23 can be generalized by summing the squared-error over all of the $N_V$ viewpoints:

$$n_g^+ = \operatorname*{argmin}_{n_g} \sum_{i=1}^{N_V} |u_{0i}' - F_i n_g|^2 + \gamma |n_g|^2 = \quad (30)$$

$$\operatorname*{argmin}_{n_g} \sum_{i=1}^{N_V} \int_V d^3 r_0 \left| u_0(0;k) \phi_i'(R_i^\dagger r_0; k) - \int_V d^3 r n_g(r) F(R_i^\dagger r_0 - r; k) \right|^2 + \gamma \int_V d^3 r |n_g(r)|^2$$

The least-squares solution can be expressed succinctly in the Fourier representation:

$$\tilde{n}_g^+(Q;k) = \frac{\sum_{i=1}^{N_V} u_0(0;k) \tilde{\phi}_i'(R_i^\dagger Q; k) \tilde{F}^*(R_i^\dagger Q; k)}{\gamma + \sum_{i=1}^{N_V} |\tilde{F}(R_i^\dagger Q; k)|^2} \quad (31)$$

To determine which spatial frequencies of $n_g$ are accessible by the instrument, we insert the measurements $u_0 \tilde{\phi}_i'(R_i^\dagger Q;k) = \tilde{F}(R_i^\dagger Q;k)\tilde{n}_g(Q)$ from Eq. 17 into Eq. 24. Doing so, we find that the reconstructed $\tilde{n}_g^+$ in terms of $\tilde{n}_g$:

$$\tilde{n}_g^+(Q;k) = \tilde{n}_g(Q;k) \frac{\sum_{i=1}^{N_V} |\tilde{F}(R_i^\dagger Q; k)|^2}{\gamma + \sum_{i=1}^{N_V} |\tilde{F}(R_i^\dagger Q; k)|^2} \quad (32)$$

The total accessible region of the Fourier space of $n_g$ is given by the sum of the $|\tilde{F}(R_i^\dagger Q;k)|^2$ as indicated in the space-invariant filter given in Eq. (32). Therefore, the measurements of φ' from multiple viewpoints can be combined to produce an estimate of $n_g$ that incorporates the spatial frequencies of $n_g$ accesible from each viewpoint, thereby enabling the synthesis of a single estimate of $n_g$ with uniform resolution in all directions.

A weighted least-squares solution can also be devised with $W_i(r_0)$ being the weights of projection i taken with the illumination beam centered at position $r_0$. Then the weighted least-squares solution can be expressed formally by $$n_g^+ = \sum_{i=1}^{N_V} (R_i^\dagger F^\dagger W^\dagger W F R_i + \gamma I)^{-1} \sum_{i=1}^{N_V} (R_i^\dagger F^\dagger W^\dagger W u_0').$$

This can be solved using sparse matrix methods such as the conjugate gradient method, but will require rotation of the working data to and from the respective coordinate systems repeatedly, which may be an undue computational burden.

A related embodiment of the invention provides a simpler, approximate solution to the weighted least-squares solution with multiple viewpoints. In this embodiment, the estimates of group refractive index from each viewpoint can be separately calculated using the weighted least-squares inverse, yielding $N_V$ estimates of the group index, one for each direction, which we call $\tilde{n}_{(i)}^+(Q;k)$. These can be combined together using the heuristic formula $$\tilde{n}_g^+(Q;k) = \frac{\sum_{i=1}^{N_V} \tilde{n}_{(i)}^+(R_i^\dagger Q; k)|\tilde{F}(R_i^\dagger Q; k)|^2}{\Gamma + \sum_{i=1}^{N_V} |\tilde{F}(R_i^\dagger Q; k)|^2} \quad (33)$$

where Γ is a regularization constant based on the noise magnitude. This estimator for $\tilde{n}_g^+$ simply weights each viewpoint by the magnitude of the spatial frequencies available from that viewpoint.

Embodiments of the Invention with Off-Axis Paraboloidal Mirrors.

In yet other related embodiments, a particularly advantageous implementation of the group refractive index confocal microscope can be realized by using two off-axis paraboloidal mirrors in place of objectives 112 and 114, of FIG. 1, that respectively focus and collect the beam transmitted through the sample. Embodiments of this sort are now described with reference to FIG. 4.

While conventional microscope objectives may be used in such a microscope, the paraboloidal mirrors have a number of advantages. First, the mirrors are simpler, because they need to correct only spherical aberration rather than other aberrations because the instrument focuses and recollects light on axis. Secondly, they are inherently achromatic because mirrors do not refract the beam. Thirdly, they produce little angular or temporal dispersion for the same reason. Fourthly, they can be immersed in the same medium containing the sample, obviating the need for windows, coverslips, or other interfaces between the sample and objective. Furthermore, the focal point and focal length of the mirrors is independent of the medium refractive index in which the mirror is immersed. Most microscope objectives cannot operate without being damaged when completely immersed in liquid media without damage, and are designed to work with a single medium such as water or immersion oil. Therefore the same paraboloidal mirrors can be used with a liquid medium that best matches the sample refractive index.

Off-axis paraboloidal mirrors are aspherical concave mirrors with an interior surface the shape of the parabola of rotation. They can be made by using a diamond-turning lathe that can produce a sub wavelength accuracy reproduction of the parabolic surface. Paraboloidal mirrors focus an incident collimated beam to a focused point. If the collimated beam is parallel to the rotation axis of the paraboloid, the focusing will be free of aberrations and, in particular, free of spherical aberration. In an off-axis parabolic mirror, part of the surface is cut away so that the focus point is not completely surrounded by the mirror surface. This enables the sample to be placed near the paraboloidal surface without obscuring the collimated beam incident onto the mirror. In a related embodiment, an on-axis paraboloid may be used but the sample will obscure the beam, and beamsplitters will likely be necessary to couple the light to and from the mirror. It is important to characterize the beam spectrum $$\tilde{B}\left(\frac{q'}{k}\right)$$

and the transfer function $$\tilde{P}\left(\frac{q'}{k}\right)$$

produced by the particular aperture shape of the parabolic mirrors so that an accurate estimate of the three-dimensional transfer function $\tilde{F}(Q;k)$ can be made. In practice, $\tilde{F}(Q;k)$ can be estimated by imaging a point (sub-wavelength) scatterer in the microscope, so that the frequency response in the resulting image is dominated by instrument limitations and not object feature size.

Figure 4:
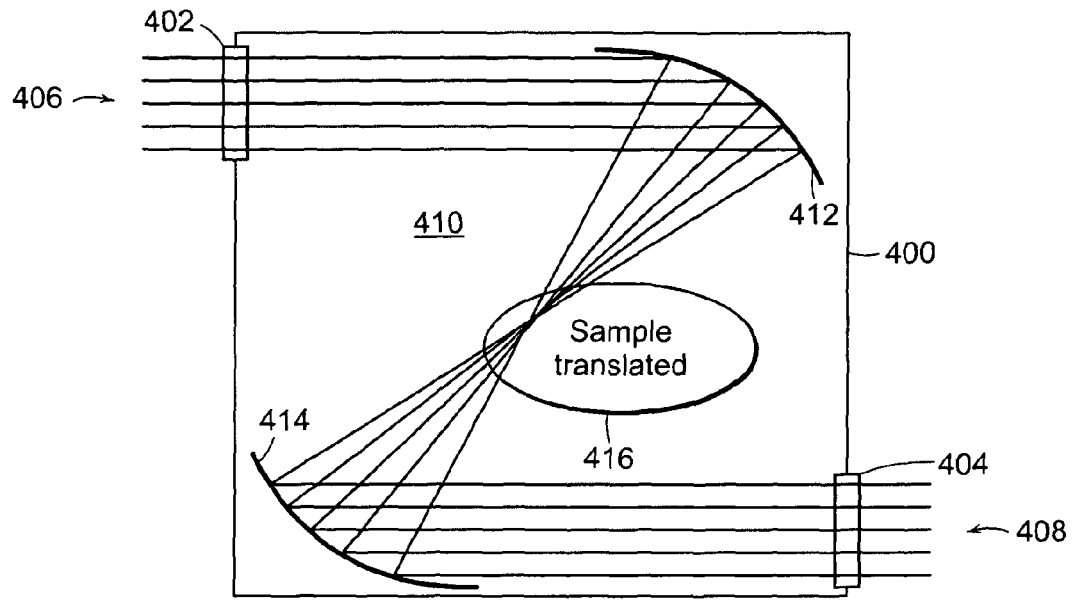
FIG. 4 shows a confocal microscope immersion tank containing off-axis paraboloid-reflectors, in accordance with embodiments of the present invention.

FIG. 4 schematically depicts an immersion tank 400 for containing the sample. The tank has two planar optical windows 402, 404 to allow the incident collimated beam 406 into the tank, and the collimated beam 408 to pass out of the tank. The tank contains a liquid 410 that immerses the paraboloidal mirrors 412, 414, the windows 402, 404, and the sample 416. This liquid is preferably chosen to be materially compatible with the sample and having a index of refraction approximately matching the average refractive index of the sample to minimize aberrations of the beam through the sample. For example, in some embodiments, various mixtures of water (n=1.33) and glycerol (n=1.47) can be used, which are non-toxic and span the range of average refractive indices typically encountered in biological tissues. The two parabolic mirrors 412, 414 are placed in the tank 400 so as to have their foci coincide and the incident beam 406 and recollimated beam 408 be parallel to the axes of their respective paraboloids, 412 and 414. The paraboloids can be placed on translation and/or rotation stages and suspended in the tank to facilitate this alignment, or they can be prealigned and then affixed to the tank wall. The sample 416 can be placed at the coinciding foci of the mirrors and suspended from a translation stage. The sample can be translated through the focus while remaining completely immersed in the medium. In an alternative embodiment, the first and the second paraboloids 412, 414 may be synchronously translated with respect to the sample 416.

Figure 5:
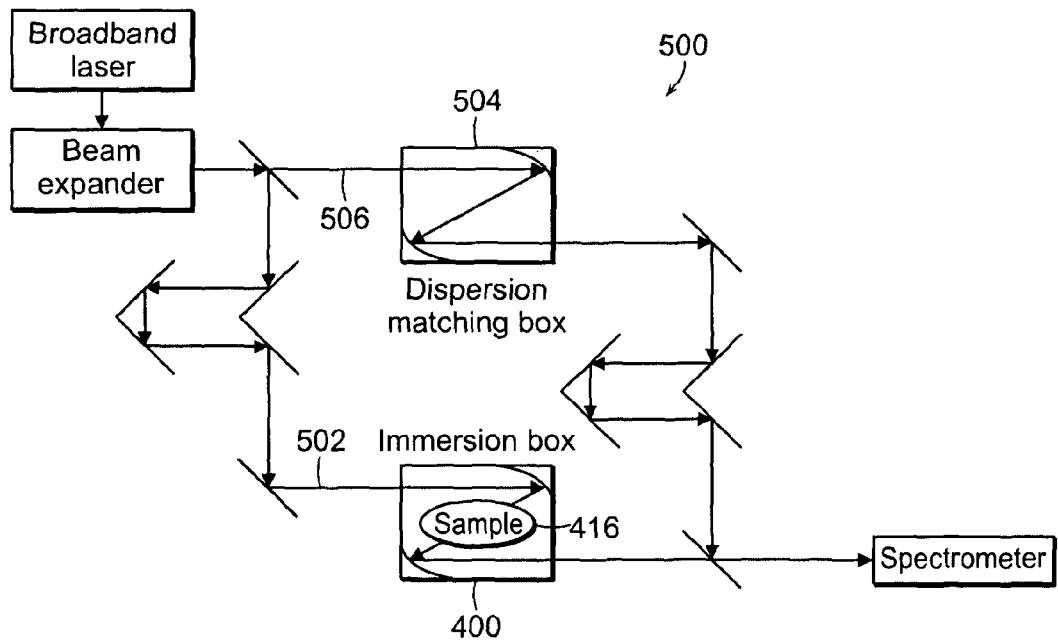
FIG. 5 schematically illustrates an off-axis paraboloid-reflector-based confocal microscope.

The overall interferometer layout is shown in FIG. 5. The interferometer, designated generally by numeral 500, is a Mach-Zehnder configuration as depicted in FIG. 1, but both arms of the interferometer have adjustable delays and immersion tanks as described above. The sample arm 502 has a sample 416 in its tank 400, while a tank 504 in the reference arm 506 is empty. Both arms of the interferometer in such embodiment are characterized by substantially identical dispersion, and a way to achieve this is to have the beam in both arms pass through identical media with the same thickness, except for the sample itself. This solution, however, is probably more expensive than necessary, because an extra pair of parabolic mirrors (within the tank 504) is required. In an alternative embodiment, all that is needed to compensate the dispersion is a tank in the reference arm containing the same medium as the immersion medium in the sample arm, omitting the parabolic mirrors performing the role of objectives in an interferometric confcal microscope of the invention. When both the sample tank 400 and the reference tank 504 are filled with the same medium and have identical windows, the reference arm tank is designed to produce the same optical path delay as the sample tank. In practice, the contribution of parabolic mirrors to overall dispersion is negligible, especially mirrors having metallic coatings, produce negligible dispersion. Therefore, the presence of the mirrors in the reference tank 504 is not generally required for the dispersion compensation, and in a specific embodiment such tank 504 does not contain mirrors. To use the Hilbert transform to infer phase from the spectral interferogram, the reference delay will need to be set so that the reference signal precedes the sample signal in time when recombined at the beam splitter before the spectrometer, but this does not produce dispersion imbalance. A small amount of residual relative dispersion between the reference and sample arms can be characterized in the spectral interferogram and digitally corrected but excessive dispersion imbalance will produce aliasing in the spectral interferogram that prevents accurate estimation of the cross-correlation signal.

Figure 6:
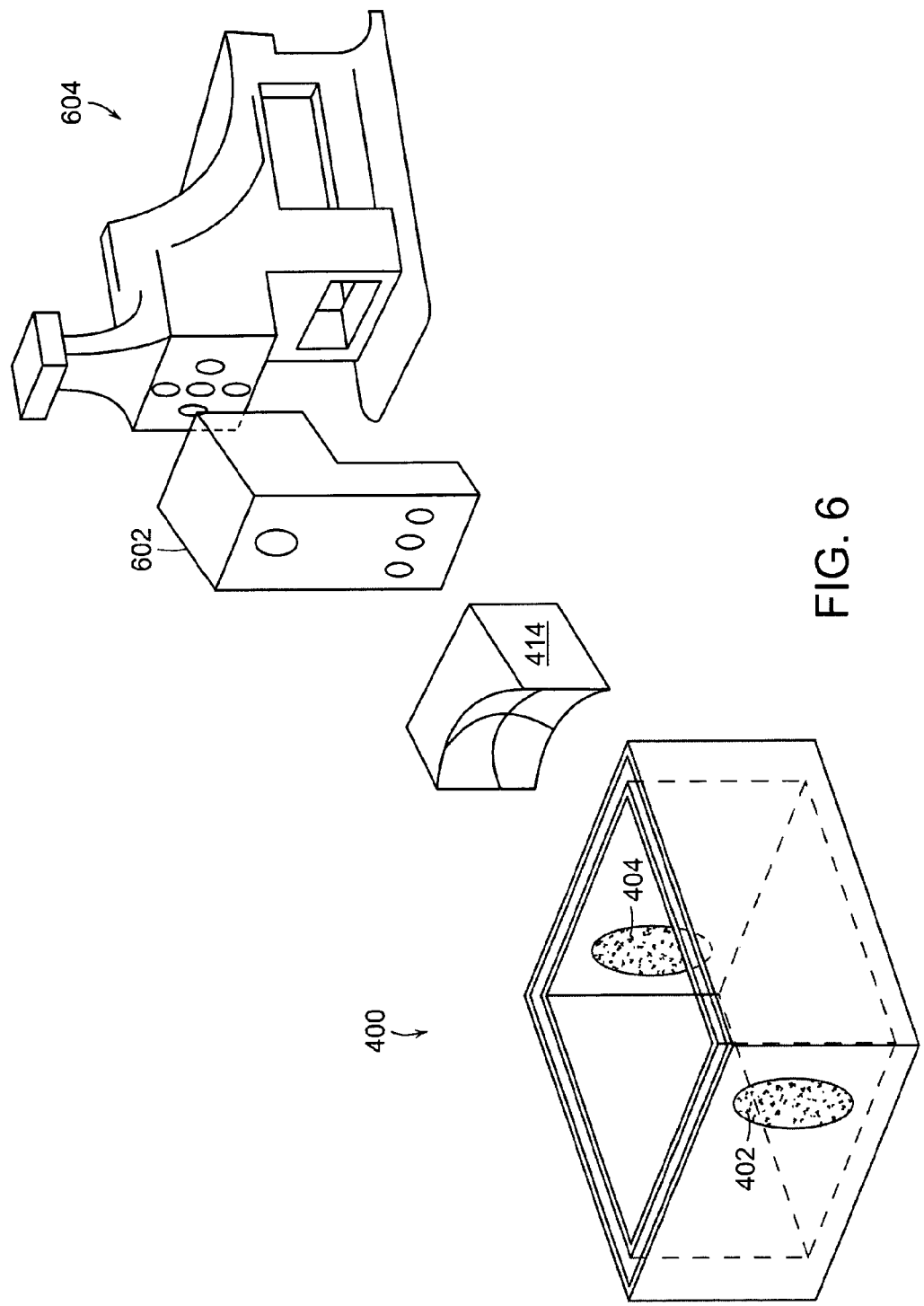
FIG. 6 is an exploded view of the immersion tank of FIG. 4, in accordance with embodiments of the present invention.

One embodiment of a tank construction is diagrammed in the exploded view of FIG. 6. The tank 400 is a hollow rectangular parallelipiped with the optical windows 402, 404 embedded in the walls (sealed to prevent medium leakage). The mirrors 414 can be mounted to an adapter block 602, which attaches the mirror to a translation stage 604, and enables the mirror to be immersed in the matching fluid while remaining rigidly coupled to the stage. A similar mount can be constructed to suspend the sample or a sample holder from a translation stage.

Optical glasses and metals that can withstand immersion in the index matching medium without dissolving are useful as a substrate for the mirror. When interrogating biological specimens, substrates that can withstand water or saline immersion with slight acidity or alkalinity are necessary. On the surface, a dielectric layer coating, or a layer of gold, platinum, rhodium, or other corrosion-resistant metal can be deposited to enhance reflectivity. Over this, a protective layer of magnesium fluoride, silicon oxide, silicon dioxide, or other transparent insoluble material can be used to enhance durability. The sample itself can be placed in a tube which can hold the sample by mild compression, a thin wire mesh screen, coverslip windows, or by embedding in agar, gelatine, or other biocompatible transparent gel.

Estimating the Monochromatic Refractive Index with the Instrument with Assistance from the Group Index Measurement.

When estimating the phase $\phi(0,r_0;k)$ of the field at the pinhole using only measurements for a single frequency k (as in Eq. 15), we noted that there is an ambiguity of a multiple of $2\pi i$ (phase wrapping) due to the application of the complex logarithm. This in partially motivated the need to measure group refractive index. In measuring the group refractive index, one may obtain an estimate of $$\frac{d\phi}{dk},$$

the imaginary part of which is the differential group optical path length between the reference and sample arms. If the refractive index of the sample is independent of k, so that $$\frac{d\tilde{n}}{dk} = 0,$$

the group optical path length of the beam transmitted through the medium is the same as the phase optical path length, which is the imaginary part of $$\frac{\phi}{k}.$$

In practice, the magnitude of the $$k\frac{d\tilde{n}}{dk}$$

component of the group refractive index $\tilde{n}_g$ tends to be small compared to $\tilde{n}$ in many biological samples, because dispersion is caused by medium absorption (as in the Kramers-Kronig rule), with the greatest dispersion at frequencies in the proximity of an absorption band. At the near-infrared wavelengths commonly used for biological imaging, absorption tends to be weak and therefore dispersion is low. Therefore, one might expect that in some biological samples the group optical path length $$\frac{d\phi}{dk}$$

and the phase optical path length $$\frac{\phi}{k},$$

while not identical, would be similar. If the magnitude of the optical path length is low $$\left(\text{perhaps less than } \frac{20\pi}{k}\right),$$

then it is likely that the two quantities will not differ by more than $$\frac{\pi}{k}.$$

Therefore an estimate of the group optical path length provides a hint of how many multiples of $2\pi i$ need to be included to produce a proper estimate of $\phi$. One should add or subtract multiples of $2\pi i$ from $\phi$ so that the imaginary part of the result is less than $\pi$ away from $$kIm\left\{\frac{d\phi}{dk}\right\}.$$

Therefore, unwrapped estimates of $\phi$ can be obtained without resorting to phase unwrapping if the group optical path length is measured. If phase unwrapping is to be used, such an estimate can be used as a starting guess for a phase unwrapping algorithm such as a weighted minimum-norm phase unwrapping method.

Embodiments of an interferometric confocal microscope, in accordance with the present invention, may also operate with monochromatic light. In this case, there will be no group delay information available to assist with phase unwrapping $\phi$. Phase unwrapping methods such as the weighted minimum-norm method can be used to unwrap $\phi$ in three dimensions. A useful choice for the weights for such a method would be the weighting function $W(r_0)=\exp[Re\phi(0,r_0;k)]$, so that samples with less transmitted power that have poorer phase estimates will not produce as large of an influence in the unwrapped phase solution. If the optical path delay is very small, with a magnitude less than $$\frac{\pi}{k},$$

then phase wraps will not occur and phase unwrapping will not be necessary. However, sufficiently thick samples will almost certainly produce a phase retardance large enough to require phase unwrapping.

In various embodiments of the present invention, the disclosed methods determining a three-dimensional mapping of the index of refraction of a sample may be implemented as a computer program product for use with a computer system. Such implementations may include a series of computer instructions fixed either on a tangible storage medium, such as a computer readable medium (e.g., a diskette, CD-ROM, ROM, or fixed disk). In alternative implementations, the computer instructions may be or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention heretofore described are intended to be merely exemplary and numerous variations and modifications will be apparent to those skilled in the art. All such variations and modifications are intended to be within the scope of the present invention as defined in any appended claims.

What is claimed is:

1. A method for imaging at least one component of a complex group refractive index of a sample, the method comprising:
 a. illuminating successive volume elements of a sample, positioned at a focus of a confocal microscope, with light from a polychromatic source;
 b. interfering a sample beam of light collected from each successive volume element positioned at the focus with a reference beam of light derived from the source to form a recombined beam for producing successive interferograms respectively corresponding to successive volume elements; and
 c. cross-correlating the sample beam and the reference beam;
 d. deriving tomographic data representing the complex group refractive index of successive volume elements of the sample.

2. A method according to claim 1, wherein the derived tomographic data includes data representing spectral dependence of phase of the sample beam of light.

3. A method according to claim 1, further comprising spatially filtering the recombined beam.

4. A method according to claim 3, wherein filtering the recombined beam includes filtering the recombined beam with a low-pass filter that is telecentric in image and object spaces.

5. A method according to claim 1, wherein deriving the tomographic data includes spectrally resolving the successive interferograms with a phase-detection member.

6. A method according to claim 1, wherein deriving the tomographic data includes deconvolving the successive interferograms.

7. A method according to claim 1, wherein illuminating each successive volume element with light from the source includes illuminating each successive volume element with infrared light.

8. A method according to claim 1, wherein illuminating successive volume elements includes illuminating successive volume elements with light having a fractional bandwidth of at least 2 percent.

9. A method according to claim 1, wherein illuminating successive volume elements includes illuminating successive volume elements with infrared light having a fractional bandwidth of at least 2 percent.

10. A method according to claim 1, wherein interfering the sample beam with the reference beam is performed with a Mach-Zehnder interferometer.

11. A method according to claim 1, wherein interfering the sample beam of light with the reference beam of light includes interfering the sample beam of light, collected in transmission through each successive volume element, with the reference beam of light.

12. A method according to claim 1, wherein the relative phase delay of light traversing the sample is free of phase-wrapping ambiguity.

13. A method according to claim 1, wherein imaging the at least one component of the complex group refractive index includes reconstructing a three-dimensional distribution of the complex group refractive index.

14. A method according to claim 13, wherein reconstructing the three-dimensional distribution of the complex group refractive index includes reconstructing a three-dimensional distribution of a single wavelength complex group refractive index.

* * * * *